(12) United States Patent
Beiski et al.

(10) Patent No.: US 9,521,973 B1
(45) Date of Patent: Dec. 20, 2016

(54) METHOD OF MONITORING PATIENTS WITH MENTAL AND/OR BEHAVIORAL DISORDERS USING THEIR PERSONAL MOBILE DEVICES

(71) Applicants: Ben Beiski, Kiryat Ono (IL); Eytan Ofry, Petach Tikva (IL); Andy Wolff, Harutzim (IL)

(72) Inventors: Ben Beiski, Kiryat Ono (IL); Eytan Ofry, Petach Tikva (IL); Andy Wolff, Harutzim (IL)

( * ) Notice: Subject to any disclaimer, the term of this patent is extended or adjusted under 35 U.S.C. 154(b) by 0 days.

(21) Appl. No.: 14/624,548

(22) Filed: Feb. 17, 2015

Related U.S. Application Data

(60) Provisional application No. 61/939,769, filed on Feb. 14, 2014, provisional application No. 61/939,790, filed on Feb. 14, 2014, provisional application No. 61/939,783, filed on Feb. 14, 2014.

(51) Int. Cl.
| | |
|---|---|
| *A61B 5/00* | (2006.01) |
| *A61B 5/16* | (2006.01) |
| *A61B 5/0205* | (2006.01) |
| *A61B 5/11* | (2006.01) |
| *A61B 5/145* | (2006.01) |
| *A61B 5/0476* | (2006.01) |
| *A61B 5/0402* | (2006.01) |
| *A61B 5/021* | (2006.01) |
| *A61B 5/024* | (2006.01) |

(52) U.S. Cl.
CPC ............ *A61B 5/168* (2013.01); *A61B 5/0205* (2013.01); *A61B 5/0402* (2013.01); *A61B 5/0476* (2013.01); *A61B 5/11* (2013.01); *A61B 5/14532* (2013.01); *A61B 5/14546* (2013.01); *A61B 5/165* (2013.01); *A61B 5/6898* (2013.01); *A61B 5/7282* (2013.01); *A61B 5/021* (2013.01); *A61B 5/024* (2013.01)

(58) Field of Classification Search
CPC ....... A61B 5/024; A61B 5/021; A61B 5/7282; A61B 5/6898; A61B 5/0402; A61B 5/0476; A61B 5/165; A61B 5/14546; A61B 5/14532; A61B 5/11; A61B 5/0205; A61B 5/168
See application file for complete search history.

(56) References Cited

U.S. PATENT DOCUMENTS

2013/0231947 A1* 9/2013 Shusterman ........ G06F 19/3443 705/2

* cited by examiner

*Primary Examiner* — George Manuel
(74) *Attorney, Agent, or Firm* — Dunlap Bennett & Ludwig PLLC

(57) ABSTRACT

A monitoring system embodying a monitoring system embodying a method of this invention for monitoring predetermined patients with mental and/or behavioral disorders by accessing, analyzing and monitoring their measured input through a plurality of sensors inherent in most personal mobile devices is provided. The measured input may represents values attributed to at least one physical behavior of the patient that is representative of a symptom of at least one mental/behavior health condition. The measured input can be used to establish a baseline and thresholds thereof that separates the at least one physical behavior into normative from ab-normative behavior for each predetermined patient.

8 Claims, 1 Drawing Sheet

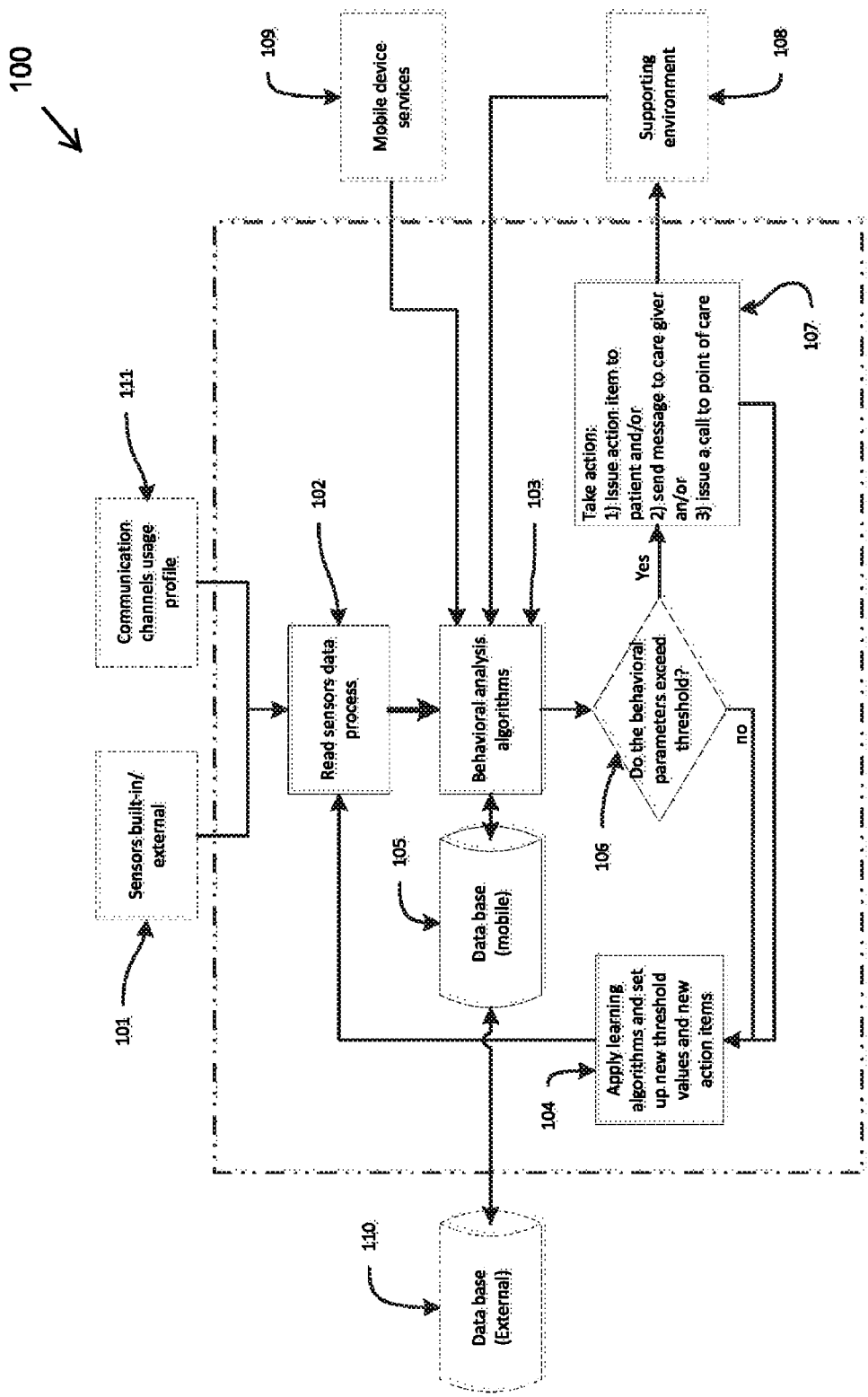

METHOD OF MONITORING PATIENTS WITH MENTAL AND/OR BEHAVIORAL DISORDERS USING THEIR PERSONAL MOBILE DEVICES

CROSS-REFERENCE TO RELATED APPLICATION

This application claims the benefit of priority of U.S. provisional application No. 61/939,769, U.S. provisional application number filed 14 Feb. 2014, 61/939,790, filed 14 Feb. 2014, and U.S. provisional application No. 61/939,783, filed 14 Feb. 2014, the contents of which are herein incorporated by reference.

BACKGROUND OF THE INVENTION

The present invention relates to mental health treatment and, more particularly, to a method of monitoring patients with mental and/or behavioral disorders using their personal mobile devices.

Mental and behavioral disorders take many forms. As a general rule, mental and behavioral disorders are associated with measurable physical behavior-related symptoms. The following is an exemplary not exhaustive list of such disorders or mental/behavior health conditions.

Attention Deficit Hyperactivity Disorder (ADHD) is a problem of not being able to focus, being overactive, not being able control behavior, or a combination of these, resulting in hyperactive and impulsive symptoms. The physical behavior-related symptoms that are measurable include, but are not limited to, fidgeting with hands or feet or squirming in seat, leaving their seat when remaining seated is expected, running about or climbing in inappropriate situations, often "on the go," as if "driven by a motor," talking excessively, and the like.

Post-traumatic stress disorder (PTSD) can be developed following a traumatic event that threatens your safety or makes you feel helpless. Most people associate PTSD with battle-scarred soldiers—and military combat is the most common cause in men—but any overwhelming life experience can trigger PTSD, especially if the event feels unpredictable and uncontrollable. Though PTSD is often accompanied by devastating functional impairment, PTSD is characterized by the presence of behavioral signs and symptoms related to intense fear, horror, and helplessness.

Mental or Behavioral Diseases (MBD) is a psychiatric disorder that results in a disruption in a person's thinking, feeling, moods, and ability to relate to others. Many MBDs, including but not limited to depression, bipolar disorder, hysteria, dementia, and the like, involve behavioral patterns or anomalies that cause distress or disability that are not developmentally or socially normative. As a result, most MBDs have behavioral representation, usually noticeable and quantifiable. Such behavioral representation differs, even through an individual's various stages of the illness/disorder.

Current commercial mobile devices including, but not limited to, smart phones, tablets, smart-watch, laptops, smart-glasses, have built-in computational components such as sensors, memory, processing units and modes of communication. Also true is the fact that mobile devices have become personal and an integral part of almost everybody's daily life, from kids, adolescents to senior citizens, as they are carried throughout the day. They are used for numerous daily tasks in addition to the countless forms of communication, social networks interaction and storage of personal data. Because of their broad penetration within the general population's every day activities, personal mobile devices have become, in essence, "integral parts of our body." Moreover, due to their deep integration into users' daily life, personal mobile devices are used "seamlessly," without the user paying attention to their presence. As a result, an individual's usage can be a reliable indication of their philological and psychiatric status, at almost any given time. When that individual is a patient suffering from mental and/or behavioral disorder, the mobile device can be used to monitor in real time, log and diagnose patients, as well as a source of corrective action.

The computational components of the mobile device can be used to establish a "normal" (or base-line) behavioral profile and log and identify in real-time a deviation from a defined threshold thereof, indicating a change in their mental state that needs attention.

As can be seen, there is a need for a method of monitoring patients with mental and/or behavioral disorders using their personal mobile devices.

SUMMARY OF THE INVENTION

In one aspect of the present invention, a method of using personal mobile devices to monitor patients with mental and/or behavioral disorders includes the steps of: accessing a plurality of sensors provided by the patient's personal mobile device; analyzing historic measured input from the plurality of sensors, wherein the measured input represents values attributed to at least one physical behavior of the patient, so as to define each physical behavior as representative of a symptom of at least one mental/behavior health condition or not; establishing a baseline from each value of the historic measured input attributed to each physical behavior defined as representative of a symptom, wherein the historic measured input is associated with normal behavior of the patient; and continuously monitoring measured input from the plurality of sensors for values that deviate by at least one threshold from the baseline.

In another one aspect of the present invention, a method of using personal mobile devices to monitor patients with mental and/or behavioral disorders includes the steps of: receiving historic measured input, wherein the measured input represents values attributed to at least one physical behavior of the patient, wherein each physical behavior is representative of a symptom of at least one mental/behavior health condition, and wherein the historic measured input is associated with normal behavior of the patient; establishing a baseline for at least one physical behavior from the values of the historic measured input; accessing a plurality of sensors provided by the patient's personal mobile device, wherein the plurality of sensors are configured to measure inputs that represent values attributed to at least one physical behavior of the patient; and continuously monitoring measured input from the plurality of sensors for values that deviate by at least one threshold from the baseline.

In yet another aspect of the present invention, a method of using personal mobile devices to monitor patients with mental and/or behavioral disorders includes the steps of: receiving a baseline of at least one value attributed to physical behavior of the patient, wherein each physical behavior is representative of a symptom of at least one mental/behavior health condition, and wherein the baseline is associated with normal behavior of the patient; accessing a plurality of sensors provided by the patient's personal mobile device, wherein the plurality of sensors are configured to receive measured inputs that represent values attributed to the at least one physical behavior of the patient; and continuously monitoring measured input from the plurality of sensors for values that deviate by at least one threshold from the baseline.

These and other features, aspects and advantages of the present invention will become better understood with reference to the following drawings, description and claims.

BRIEF DESCRIPTION OF THE DRAWINGS

FIG. 1 is an exemplary diagram of a mobile device environment in which specific embodiments of the present invention may be implemented.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a monitoring system embodying a method of this invention for monitoring predetermined patients with mental and/or behavioral disorders by accessing, analyzing and monitoring their measured input through a plurality of sensors inherent in most personal mobile devices. The measured input may represents values attributed to at least one physical behavior of the patient that is representative of a symptom of at least one mental/behavior health condition. The measured input can be used to establish a baseline and thresholds thereof that separates the at least one physical behavior into normative from ab-normative behavior for each predetermined patient.

The present invention defines a monitoring system 100 embodying a method of this invention for monitoring patients with mental and/or behavioral disorders using their personal mobile devices. The monitoring system 100 may include at least one computer with a user interface. The computer may include at least one processing unit having a form of memory including, but not limited to, a desktop, laptop, mobile device and smart device, such as, a tablet, smart phone, smart watch and the like. The computer includes a program product including a machine-readable program code for causing, when executed, the computer to perform steps. The program product may include software which may either be loaded onto the computer or accessed by the computer. The loaded software may include an application on a mobile device. The software may be accessed by the computer using a web browser. The computer may access the software via the web browser using the internet, extranet, intranet, host server, internet cloud and the like.

Referring to FIG. 1, illustrates a mobile device environment in which specific embodiments of the monitoring system 100 may be defined as: 101 Plurality of Sensors—mobile device built-in sensors or external sensors connected to the mobile device via wired or wireless connections; 102 Mobile device software modules that can read the sensors data; 103 Mobile device software modules that can analyze the behavior using custom made algorithms; 104 Mobile device software modules that can update the thresholds and the action items based on accumulated data coming from the sensors, and internal and external data bases; 105 Mobile device data base that can retrievably store all the necessary information of the patients, the former sensor's data, threshold, action items, medications, schedule, and more; 106 Decision software modules that can determine if the recently received data exceeds the defined thresholds; 107 A list of action items to be taken by the mobile device if recent analysis results in exceeding the threshold(s); 108 The patient's supporting environment: his/her parents, care giver, nursing assistance, teacher, kinder garden teacher, nurse, doctor, therapist, etc.; 109 Mobile device services including operating system services, and other software modules installed on the mobile device; 110 Data base from external sources such as the patient's personal information; and 111 Communication channels usage profile is aimed at giving information on usage profile of communication channel such as telephone, text and media messages, social networks participation, etc., and wherein all the above mentioned components are in readable communication with each other or portions thereof.

In order to detect and identify ab-normal behavior (of the mobile device user), the monitoring system 100 may measure (102), periodically, any measurable parameter that represents a characteristic of mental or behavioral health or a symptom of a mental health condition. The plurality of sensors (101) built-in in the mobile device or added-on and communication channels (110), may provide their input periodically to the behavioral analysis algorithms (103). The behavioral analysis algorithms (103) may perform the analysis based on additional inputs:

a) data coming from external data base (110) that includes personal medical files, personal data, scientific data and algorithms;

b) data coming from a local data base at the mobile device (105), memory personal medical files, personal data, scientific data and algorithms;

c) user's supporting environment input (108) namely his/her parents, care giver, medical therapist, can provide input such as, if the user took medications that may influence his/her behavior? When? What dosage? Is he/she ill? Or other relevant data that may affect the user's behavior; and d) mobile device services (109) such as the operating system services (time, day, memory etc.) or other applications in use (if he/she is playing a specific game that affect their behavior?).

The output of the Behavioral analysis algorithm (103) are momentary behavioral indices (parameters) that may compare vs. the predetermined patient's normal (base-line) behavior indices and/or thresholds (parameters) in (106) a module that makes the comparison and issues indications if the behavior is with the norm or exceeding it. If the outcome of module (106) is not within the norm, action items are taken. Among those action items may be:

a) an indication to the user (vocal, textual, media), suggestion to the user (calm down, go drink water), etc.;

b) Biofeedback to the user in a form of "serious games", instructions, guidance;

c) send message (voice/text/media) to the care givers (he/she needs your attention, needs your help, etc.);

d) send message (voice/text/media) to the professional/consulting point of care, that may advise to take medication, seek medical attention; and e) or any combination thereof.

The supporting environment (108) can be his/her parents, friends, teacher, kindergarten, care giver, nurse, medical doctor, medical team, psychologist, etc.

In order to keep the threshold dynamic, updated and personal, the accumulated data may be inputted in a learning algorithms module (104) that updates, if needed, the thresholds, action items and values may be used in the future analysis at the behavioral analysis algorithms (103). The learning algorithms module 104 may include providing at least one adaptive machine learning algorithm configured to define the baselines and thresholds based on in part the logged measured input.

Because of their deep integration into daily life and their inherent computational components the personal mobile device can be used to reliably indicate the user's philological and psychiatric status, at almost any given time. The computational components may be used to establish a "normal" (or base-line) behavioral profile, from which thresholds can be defined. Moreover, the computational components can be used to log and identify in real-time a deviation from said thresholds, indicating a change in their mental state that needs attention.

The computational components inherently found on personal mobile devices bought off the shelf include a plurality of sensors 101 that can measure and collect input that represents characteristics of mental health condition and/or behavior. In other words, the plurality of sensors 101 may be analyze historic measured input from the plurality of sensors, wherein the measured input may represent values attributed to at least one physical behavior of the patient. If any such physical behavior can be defined as representative of a symptom of at least one mental health condition, then the associated values of the underlying measured input can be used to establish a baseline for physical behavior that is symptomatic of mental health conditions. The characteristics of the physical behavior can be logged during a normal state of a predetermined patient so that the baseline is normative, and so sufficient deviations from the baseline(s) may be deemed indicative of abnormal behavior, a change in behavior or mental state beyond and the like that needs attention of the predetermined patient's supporting environment 108. The predetermined patient's supporting environment 108 may include parents, care giver, nursing assistance, teacher, kinder garden teacher, nurse, doctor, therapist, and the like.

The sufficient deviations for each symptom of mental/behavior health conditions may be deemed a threshold. Thresholds may be defined as a limit of what is physical behavior the separates "normal" and abnormal mental health-related behavior, and such limits may be supported by the DSM, ICD and/or other professional accepted parameters in view of the predetermined patient history or historic measured input. In certain embodiments, historic measured input may be associated with a normative period and so normative baseline.

In an alternative embodiment, the baseline may be established by an external database 110. The external database 110 may include direct input from the support environment 108, exportable external sources such as the patient's personal information, his/her files at the medical services provider, files from the education system, the medications' manufacturer, games' vendor and any other information that may be needed to run the monitoring system 100.

The following is an exemplary, but not exhaustive, list of the plurality of sensors 101, externally added and/or that can be found in off-the shelf personal mobile devices and the related mental health behavior characteristics(s) that can be measured and collected, as well as additional sensors can be added to the mobile device.

a) Microphone—whereby vocal characteristics can be measured, such as a baseline vocal pitch, volume level, word per minute rate of speaking and the like, which in turn can be used to log and identify if the mobile device user is significantly deviating from the baseline when, for example, talking with a higher pitch, yelling, whispering, talking faster, talking slower due to a change in behavior or mental state beyond a related threshold;

b) Touch screen—whereby haptic characteristics can be measured, such as a baseline rate and a force of touch, touch capacitance, touch movements, touch with more than one finger, and the like, which in turn can be used to log and identify significant deviations in said haptic characteristics due to a change in mental state beyond a related threshold;

c) Keypad/keyboard—whereby keying characteristics can be measured such as the speed of typing, accuracy of typing, repetitive and/or meaningless input, which in turn can be used to log and identify significant deviations in said keying characteristics associated with a change in behavior or mental state beyond a related threshold;

d) Gyro sensor—whereby motion-related characteristics can be measured, such as recognition of hand movements (when the user is holding the mobile device in their gesticulating hand), general rotational state based on three axis, which in turn can be used to log and identify changes in said motion-related characteristics associated with a change in behavior or mental state beyond a related threshold;

e) Motion sensors, such as accelerometers, hall effect sensors and the like, can be used to measure motion-related characteristics of the user of the mobile device such as the rate, consistency and direction of the user's movement, which in turn can be used to log and identify changes to the motion-related characteristics associated with a change in behavior or mental state beyond a related threshold;

f) Light sensors, such as RGB light sensors, ambient light sensors, back illuminated sensor and the like, can be used to measure motion-related characteristics of the user of the mobile device, which in turn can be used to log and identify changes to the motion-related characteristics associated with a change in behavior or mental state beyond a related threshold; and g) Positioning sensors, such as proximity sensors, barometer, temperature, GPS sensors, NFC, and the like, can be used to measure the location of the mobile device user so as to log and identify any changes to the user's location associated with a change in behavior or mood beyond a related threshold.

h) Camera, such as front or back camera to measure usage profile (number of "selfies", identifies face, impression changes to identify mode change, and the like;

i) Additional, non-built-in sensors can provide input. The connection to the sensors can be using wire or wireless communication with the mobile device. Such as:
 i) EEG (Electroencephalography)
 ii) ECG (electrocardiography)
 iii) Heart Rate
 iv) Blood pressure
 v) Glucose level
 vi) Cholesterol level
 vii) Blood components that affect the mental status such as Sodium, Potassium, Calcium, hemoglobin, etc.

Many of the above-mentioned mental and behavioral symptoms have representations measurable by the above-mentioned plurality of sensors found in off-the shelf personal mobile devices or that can be added to. For instance, the microphone may measure voice alterations indicative of ADHS, PTSD or MBD symptoms, the touch screen sensor may measure touch screen activity indicative of symptoms, and the keypad/keyboard sensor may measure usage deviating from the user's behavioral profile that is consistent with symptoms, movement in space and movement of the arms (which may hold the mobile device) may be measured by the gyro sensor so as to indicate the user's breaking of a related threshold. Moreover, frequent calls or texting or other media content posting to other individuals, activity in social networks (or the opposite—no calls or texting to other individuals, no posting of media content, no activity in social networks) may be probative of symptoms. Add-on sensors such as glucose meter can indicate of hypoglycemia that affects behavior, fast heart rate can indicate an anxiety and restless status, etc.

The computer-based monitoring system 100 and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or portions of the present invention may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the invention as set forth in the following claims.

What is claimed is:

1. A method of using a personal mobile device to monitor a patient having a predetermined mental and/or behavioral disorder comprising the steps of:

logging historic measured input from at least one of a plurality of sensors provided by the personal mobile device, wherein the measured input represents values attributed to at least one physical behavior of the patient, and wherein the DSM defines the at least one physical behavior as representative of a symptom of the predetermined mental/behavior health disorder;

establishing a baseline of measured input from the logged historic measured input when the historic measured input is associated with normal behavior of the patient as defined by a supporting environment of the patient;

establishing a threshold of measured input based in part on the baseline of measured input and a deviation in values attributed to the at least one physical behavior, wherein the DSM defines the deviation in values as indicative of an abnormal mental state of the patient for the predetermined mental and/or behavioral disorder; and comparing a current measured input from the at least one of the plurality of sensors so as to determine if the current measured input exceeds the threshold of measured input, so as to monitor the patient.

2. The method of claim 1, further including effectuating at least one of a plurality of action items if the current measured input exceeds the threshold of measured input.

3. The method of claim 2, wherein the plurality of action items includes an audio or visual suggestion through the personal mobile device and a transmission of a message to the supporting environment.

4. The method of claim 1, wherein the baseline of measured input is received from an external database.

5. The method of claim 1, wherein the at least one of the plurality of sensors includes a microphone, and wherein the at least one physical behavior is vocal characteristics.

6. The method of claim 1, wherein the at least one of the plurality of sensors includes a touch screen, and wherein the at least one physical behavior is haptic characteristics.

7. The method of claim 1, wherein the at least one of the plurality of sensors includes a keypad or keyboard, and wherein the at least one physical behavior is key characteristics.

8. The method of claim 1, wherein the supporting environment is a doctor of the patient.

* * * * *